(12) United States Patent
Blanchette et al.

(10) Patent No.: US 6,811,255 B2
(45) Date of Patent: Nov. 2, 2004

(54) PROTECTIVE EYEWEAR ASSEMBLY

(75) Inventors: Luc Blanchette, Montreal (CA); Eric LaPointe, Montreal (CA)

(73) Assignee: Cabot Safety Intermediate Corporation, Newark, DE (US)

(*) Notice: Subject to any disclaimer, the term of this patent is extended or adjusted under 35 U.S.C. 154(b) by 0 days.

(21) Appl. No.: 10/648,754

(22) Filed: Aug. 25, 2003

(65) Prior Publication Data

US 2004/0141149 A1 Jul. 22, 2004

Related U.S. Application Data

(63) Continuation of application No. PCT/US02/05812, filed on Feb. 25, 2002.

(51) Int. Cl.[7] .................................................. G02C 1/00
(52) U.S. Cl. ............................ 351/83; 351/86; 351/154
(58) Field of Search ........................... 351/83–86, 111, 351/120, 154

(56) References Cited

U.S. PATENT DOCUMENTS

| | | | | |
|---|---|---|---|---|
| 4,405,212 A | * | 9/1983 | Cooper | 351/43 |
| 5,069,541 A | * | 12/1991 | Holmes et al. | 351/86 |
| 5,227,817 A | * | 7/1993 | Simioni | 351/80 |
| 5,796,461 A | * | 8/1998 | Stepan | 351/106 |

* cited by examiner

*Primary Examiner*—Huy Mai
(74) *Attorney, Agent, or Firm*—Cantor Colburn LLP

(57) ABSTRACT

The protective eyewear assembly described comprises a frame having right and left portions defining respective right and left apertures and a central bridging portion, and a protective lens piece adapted to be mounted to the lens piece between the upper and lower edges of the frame. The lower edge of the frame has a retaining wall for retaining the lens therein while the upper edges of the frame and the lens piece have cooperating portions to secure the lens to the frame. The frame may be made of flexible plastic material to enable a snap-in engagement and a snap-out disengagement of the lens to and from the frame.

12 Claims, 6 Drawing Sheets

PROTECTIVE EYEWEAR ASSEMBLY

CROSS REFERENCE TO RELATED APPLICATIONS

The present application claims priority to International Patent Application No. PCT/US02/105812, filed Feb. 25, 2002, the entire contents of which are specifically incorporated herein by reference, which claims priority to Canadian Patent Application No. 2,337,928, filed Feb. 23, 2001, the entire contents of which are specifically incorporated herein by reference.

BACKGROUND

It is not at all unusual for a lens and/or an ear stem of protective eyewear to break during industrial use. Such occurrences of breakage generally require that a user discard the entire eyewear and replace it with a new pair.

The industry also lacks a protective eyewear selection that can comfortably accommodate different sizes. This lack of comfort and adjustability is particularly felt when workers must wear such protective eyewear during long hours of industrial work. There is therefore a need in the art for eyewear that solves the problems attendant to breakage of the eyewear. At the same time, there is a need for eyewear that provides comfort to the wearer during hours of industrial use.

SUMMARY

The presently described eyewear overcomes and alleviates the above-described and other disadvantages of the prior art by providing a protective eyewear assembly which is adapted to be both comfortably worn and adjusted to fit different users. The presently described eyewear also overcomes and alleviates the above-described and other disadvantages of the prior art by providing eyewear for industrial use whose components can be easily mounted and/or dismounted in the event of any of its components being damaged.

The present eyewear therefore relates to a protective eyewear assembly comprising a frame having right and left portions defining respective right and left apertures and a central bridging portion, and a protective lens piece adapted to be mounted to the lens piece between the upper and lower edges of the frame. The lower edge of the frame has a retaining wall for retaining the lens therein while the upper edges of the frame and the lens piece have cooperating portions to secure the lens to the frame. The frame may be made of flexible plastic material to enable a snap-in engagement and a snap-out disengagement of the lens to and from the frame.

In one embodiment, the eyewear further comprises a pair of ear stems respectively mounted at an upper edge extremity of the right and left portions to pivot between an inwardly folded position and an outwardly ear contacting position.

In another embodiment, the protective lens piece comprises a transparent plastic material defining a unitary arcuate body. The lens piece is adapted to be mounted to and rearwardly of the frame between the upper edge extremities of the frame. The lens piece includes a pair of right and left sight regions and a central bridging region. The right and left sight regions and the bridge region include an upper edge adapted to be received beneath the upper edge surface of the right and left portions and the central bridging portion, and a lower edge adapted to be supported on the lower edge lens supporting surface of the right and left portions and the bridging portion of the frame.

In another exemplary embodiment, the lower edge lens supporting surface includes means to retain the lens when mounted to the frame and wherein the upper edge surface of the right and left portions of the frame and the upper edge of the right and left regions of the lens include cooperating means to secure the lens to the frame.

In another exemplary embodiment, a flexible plastic material of the frame enables a snap-in engagement and a snap-out disengagement of the securing means to and from one another.

In another exemplary embodiment, the cooperating means comprises a slot means on the upper surface of the right and left portions of the frame and of projection means on the upper edge of the right and left regions of the lens.

In another exemplary embodiment, the retaining means comprises a rib means extending along an outer edge of a portion of the lower edge supporting surface of the right and left portions of the frame.

Other objects and further scope of applicability of the present invention will become apparent from the detailed description given hereinafter. It should be understood, however, that this detailed description, while indicating preferred embodiments of this invention, is given by way of illustration only since various changes and modifications within the spirit and scope of the invention will become apparent to those skilled in the art.

DESCRIPTION OF PREFERRED EMBODIMENTS

Figure 1:
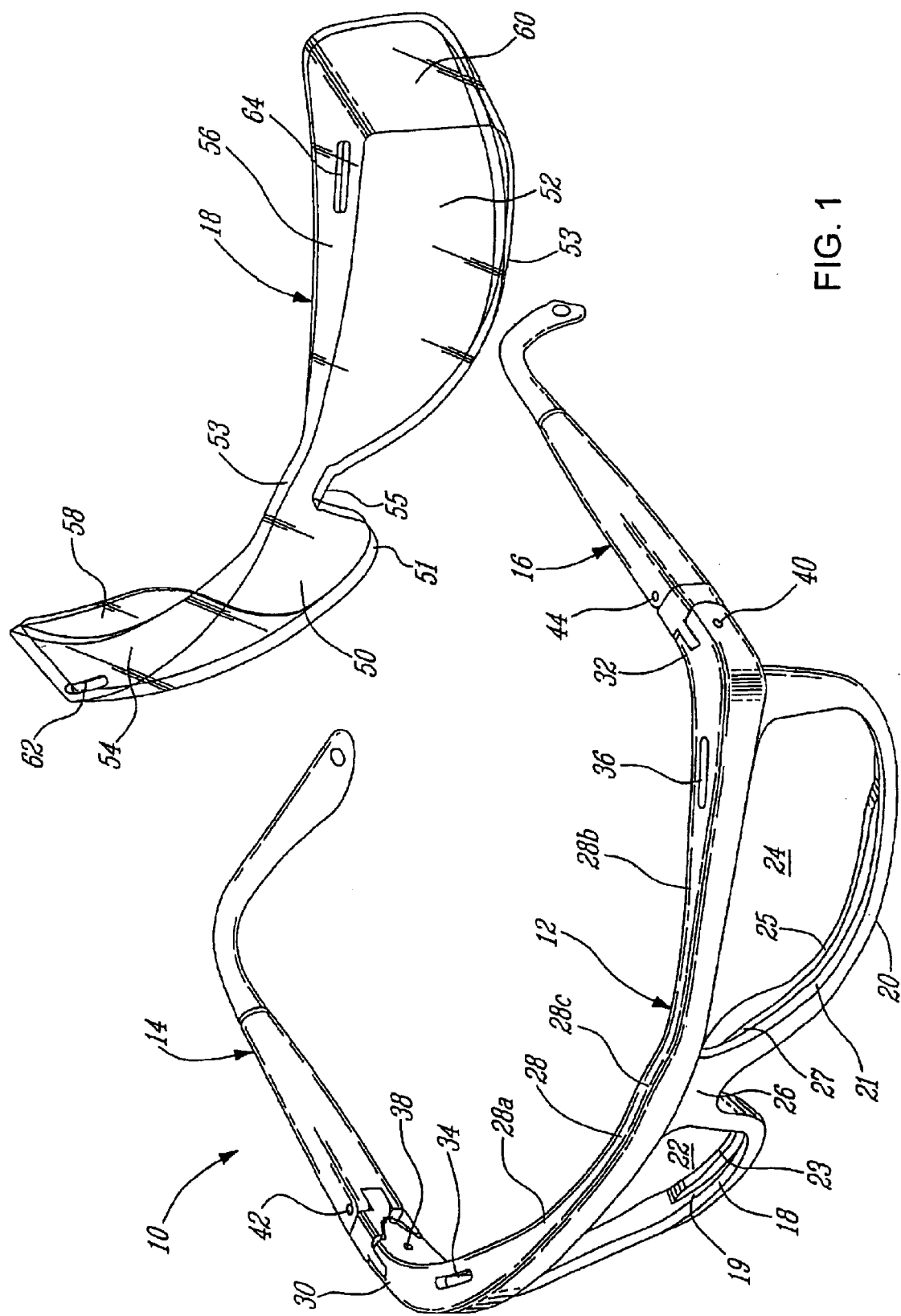
FIG. 1 is an exploded top perspective view showing an exemplary embodiment of the present protective eyewear assembly.
Figure 2:
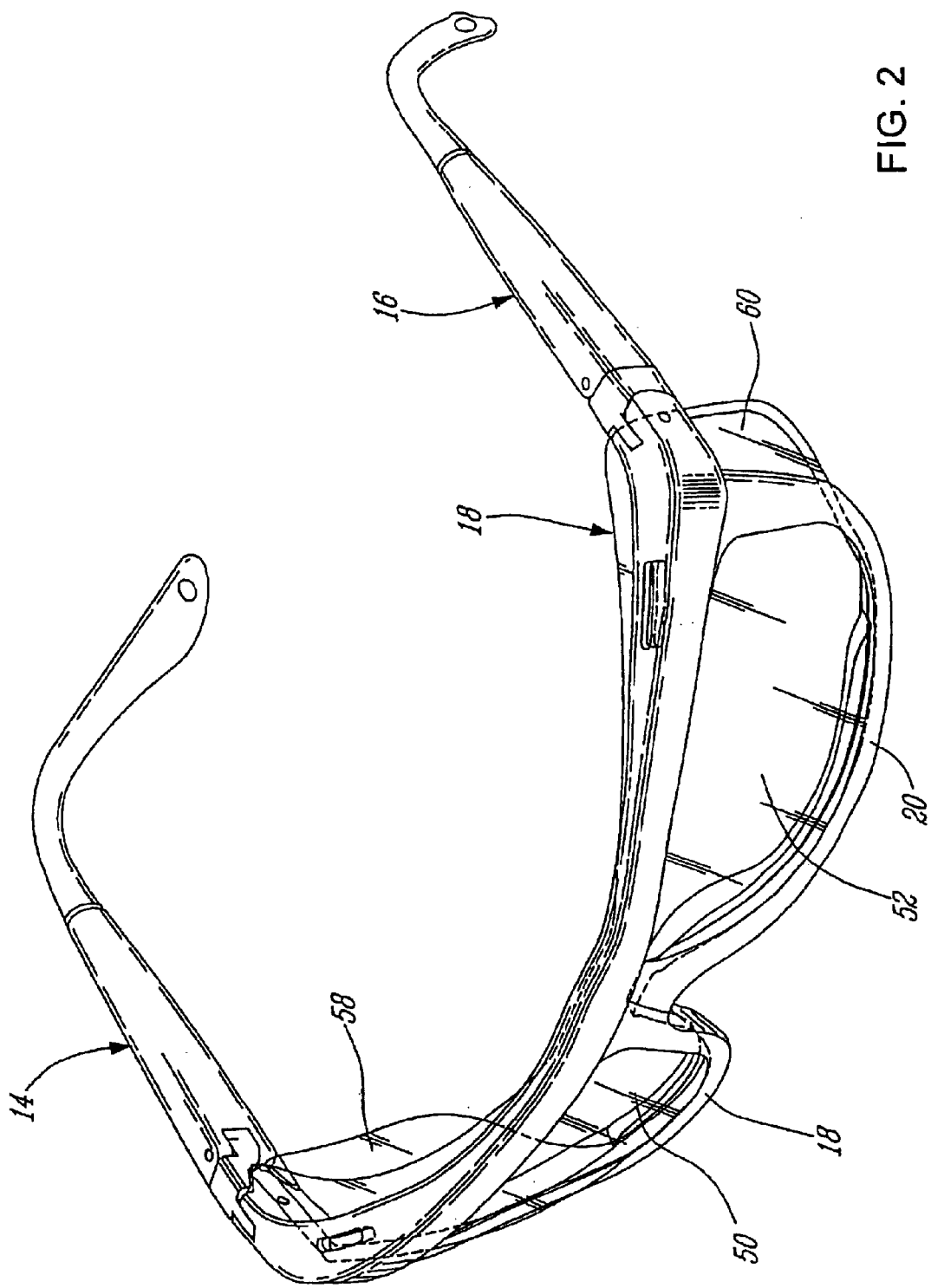
FIG. 2 is a top perspective view of the assembled eyewear.
Figure 3:
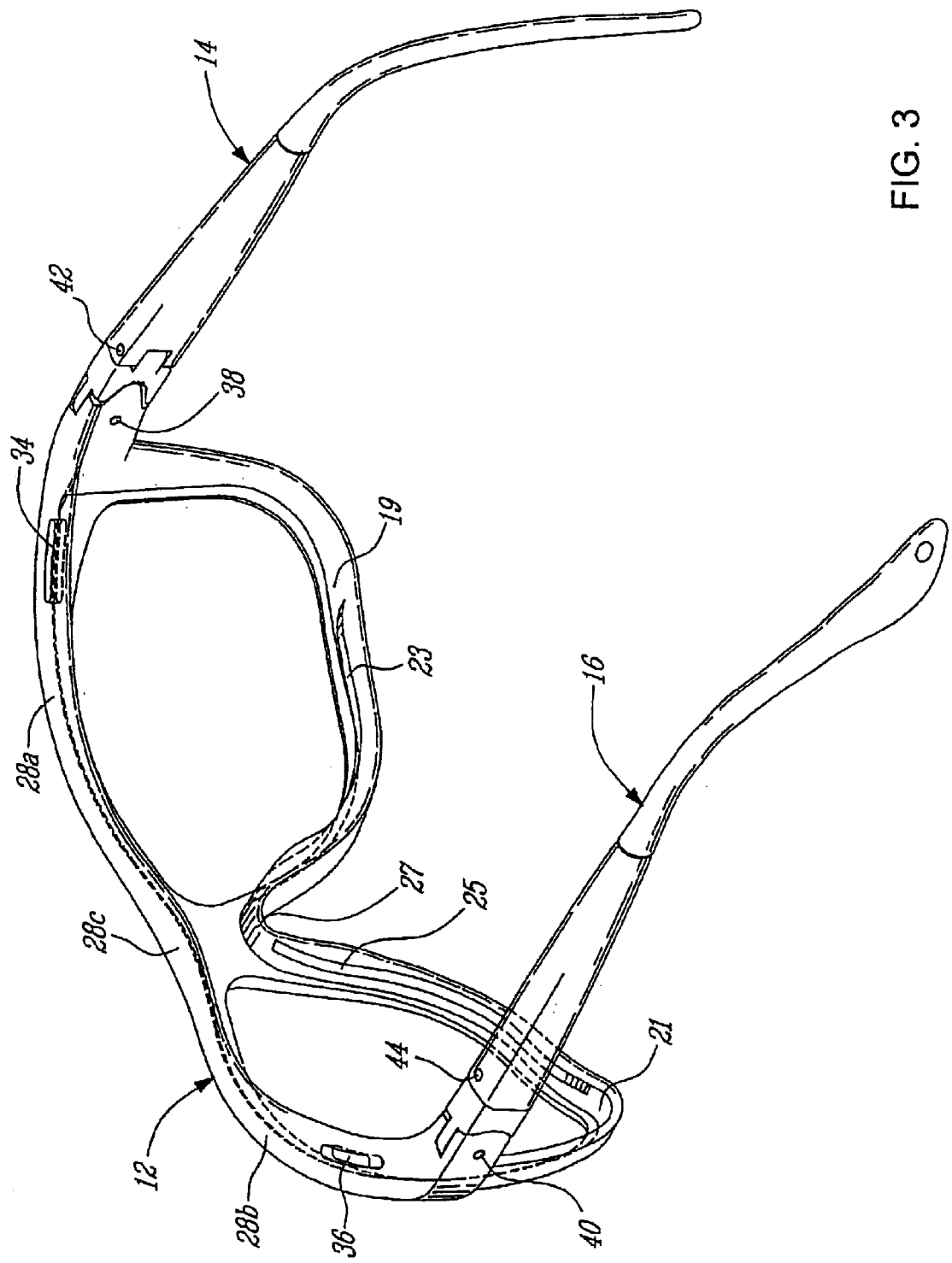
FIG. 3 is a rear perspective view of the frame with the lens shown in dotted lines.
Figure 4:
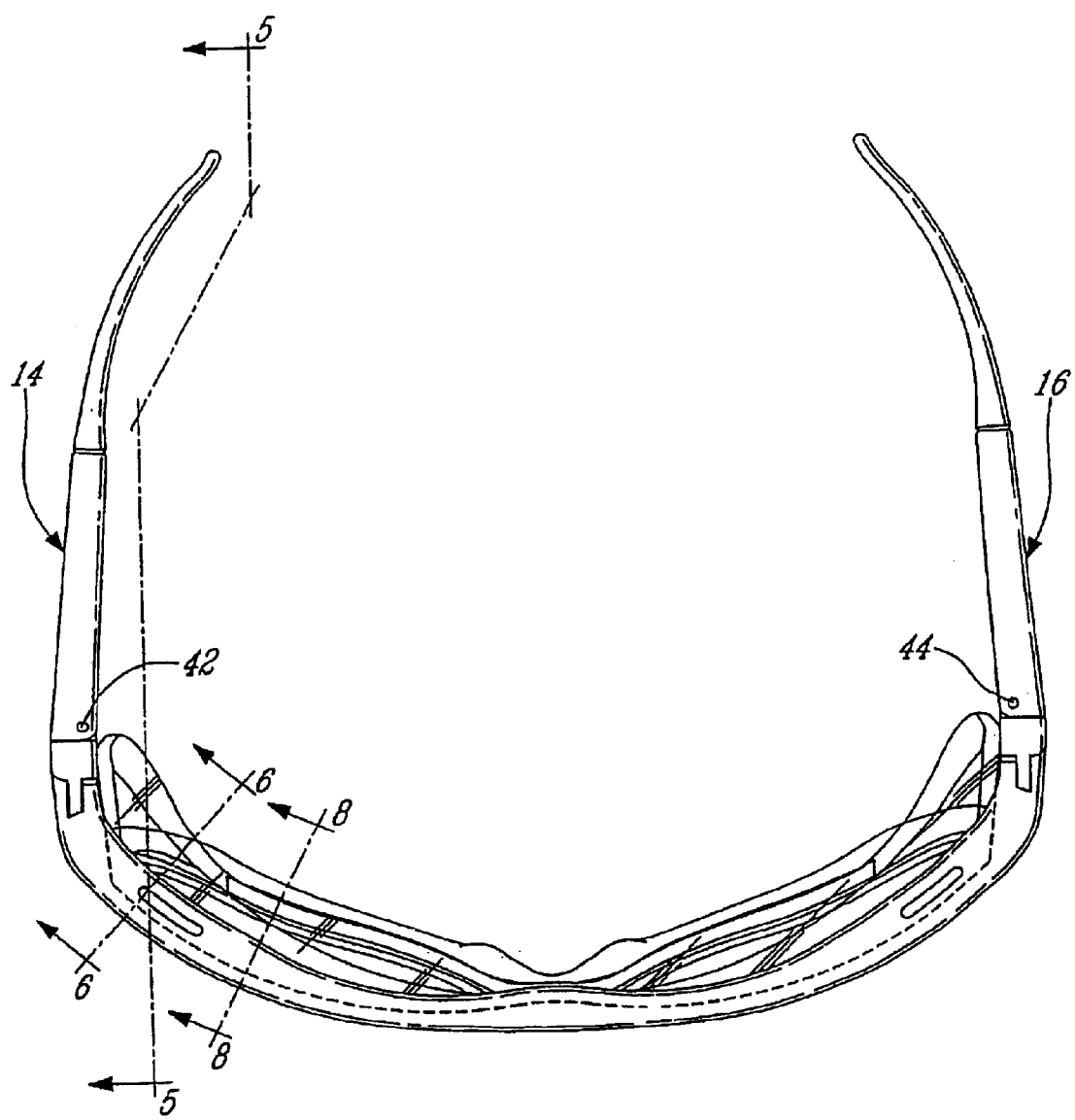
FIG. 4 is a top view thereof.
Figure 5:
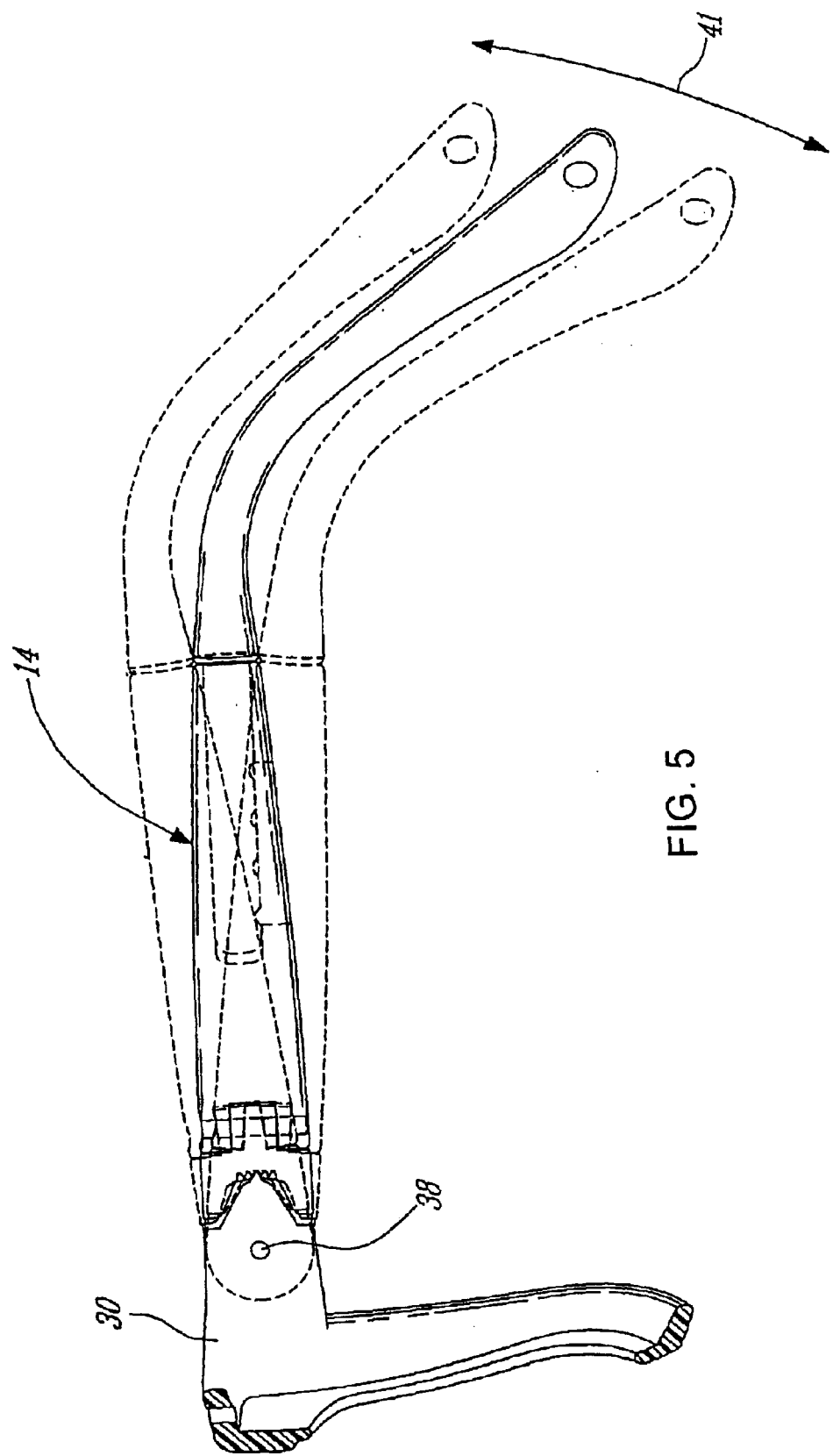
FIG. 5 is a cross-sectional view taken along lines 5—5 of FIG. 4.
Figure 8:
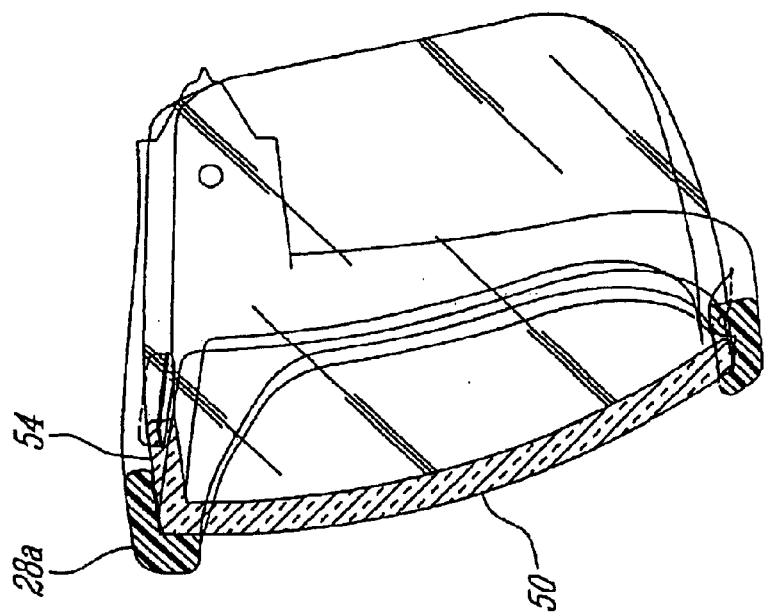
FIG. 8 is a cross-sectional view taken along lines 8—8 of FIG. 4.

Referring to FIGS. 1–8, there is shown the various exemplary components forming the protective eyewear assembly, generally denoted 10, of the presently described exemplary eyewear. It includes a frame 12, a pair of ear stems 14 and 16 and a lens piece 18.

The exemplary frame 12 has right and left portions 18 and 20 defining respective right and left apertures 22 and 24, and a central bridging portion 26 extending therebetween. The upper edge 28 of the lens has a given width and consists of three sections 28a, 28b and 28c. The under surface of the upper edge defines a lens receiving area. The width of the upper end 28 is the smallest at the central section 28c and gradually increases as it curves outwardly and rearwardly towards the extremities of the end sections 28a and 28b. These extremities of the exemplary lens define rearward extensions 30 and 32 to which are pivotly connected the ear stems 14 and 16, respectively. The end sections 28a and 28b of the upper edge of the lens 12 each display an elongated slot 34 and 36. In an exemplary embodiment, the lens 12 is made of a flexible plastic material Exemplary ear stems 14 and 16 are pivotly connected to the rearward extensions 30 and 32 through a first pin 38, 40 enabling the ear sterns to move in a vertical plane and indicated by arrow 41 in FIG. 5 and through a second pin 42, 44 in order to allow the ear stem to be pivoted between an inwardly folded position and an outwardly extending ear contacting position. While the various figures show exemplary pivotal arrangements, it should be recognized that alternate pivoting mechanisms may be employed within the scope of the present disclosure, as may be known in the art.

The lower edges of the right and left frame portions 18 and 20 as well as the central bridging portion 26 define lens supporting surfaces 19, 21 and 27. Surfaces 19 and 21 include rear walls 23 and 25 that extend from about the middle of surfaces 19 and 21 and up to the lower surface 27 of the bridging portion 26.

In an exemplary embodiment, the lens 18 comprises a unitary arcuate body made of transparent plastic material. It includes a pair of right and left sight regions 50 and 52 and a central bridging region 53. The upper edges of the regions 50 and 52 each display a flat horizontal surface 54 and 56 which progressively increases in width and in a curved manner from the central portion 54 to the outer extremities which define side shields 58 and 60. The upper surfaces 54 and 56 each displays a rectangular-shaped projection 62 and 64 which are dimensioned so as to snuggly fit into the elongated slots 34 and 36 of the lens frame.

To assemble the lens piece 18 to the frame 12, the lower edges 51 and 53 of the sight regions 50 and 52 are placed on their corresponding surfaces 19 and 21 of the frame with the lower edge 55 of the lens piece resting on surface 27 of the frame. Due to the flexibility of the material of the frame, the upper part of the lens is forcingly moved to the frame so that the top surfaces 54 and 56 of the lens are positioned beneath the under surfaces of the upper edge sections 28a and 28b of the frame with the top edge 54 of the lens being received under the upper edge section 28c of the frame. The presence of projections 62 and 64 of the lens provide some hindrance to such entry. However, the flexibility of the material of the frame will cause a slight upward movement of the frame sections 28a and 28b so that the projections 62 and 64 will slide along the undersurfaces of sections 28a and 28b until they reach and engage the slots 34 and 36. Thus, there is achieved a snap-in engagement of the lens to the frame.

Disengagement of the lens and the frame from one another is achieved in the reverse manner; in other words a slight upward force on the upper edges of the frame will free the projections 62 and 64 from their respective slots 34 and 36 and the lens is separated.

Figure 7:
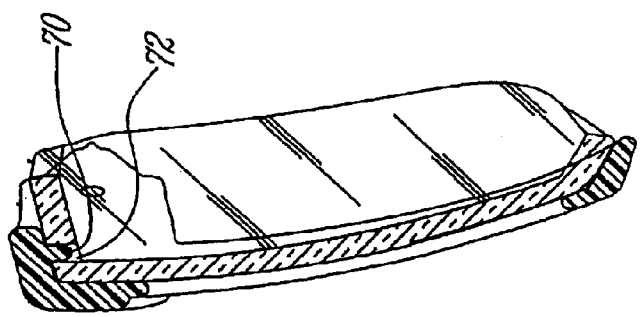
FIG. 7 is a cross-sectional view similar to that of FIG. 6, showing another exemplary embodiment of the present eyewear.
Figure 6:
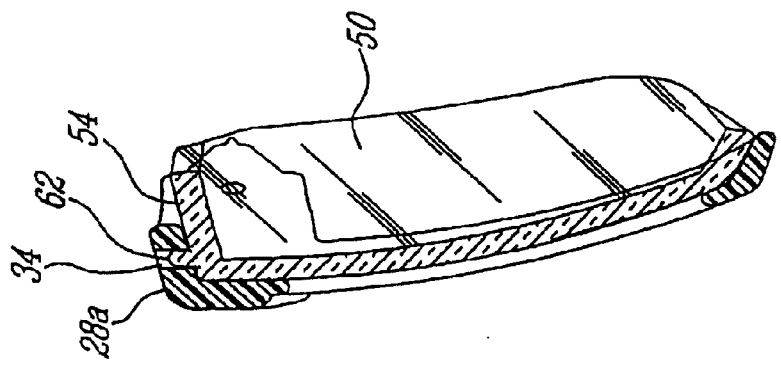
FIG. 6 is a cross-sectional view taken along lines 6—6 of FIG. 4.

While the invention has been described with reference to an exemplary embodiment, it will be understood by those skilled in the art that various changes may be made and equivalents may be substituted for elements thereof without departing from the spirit or scope of the invention. For example, as illustrated in FIG. 7, the lens/frame engagement may be formed with a projection 70 provided on the upper edge of the frame and engageable with a corresponding slot 72 in the upper edge of the lens. In addition, many modifications may be made to adapt a particular situation or material to the teachings of the invention without departing from the essential scope thereof.

Therefore, it is intended that the invention not be limited to the particular embodiment disclosed as a best mode contemplated for carrying out the invention, but that the invention will include all embodiments falling within the scope of the appended claims.

What is claimed is:

1. A protective eyewear assembly comprising:

a frame having right and left portions defining respective right and left apertures and a central bridging portion between said right and left portions; said right and left portions and said bridging portion displaying an upper edge lens receiving surface and a lower edge lens supporting surface; said frame being made of flexible plastic material;

a pair of ear stems respectively mounted at an upper edge extremity of said right and left portions to pivot between an inwardly folded position and an outwardly ear contacting position; and a protective lens piece made of transparent plastic material defining a unitary arcuate body and adapted to be mounted between said upper edge extremities of said frame, said lens piece including a pair of right and left sight regions and a central bridging region; said right and left sight regions and said bridge region displaying an upper edge adapted to be received beneath said upper edge surface of said right and left portions and said central bridging portion , and a lower edge adapted to be supported on said lower edge lens supporting surface of said right and left portions and said bridging portion of the said frame;

wherein said lower edge lens supporting surface includes means to retain said lens when mounted to said frame and wherein said upper edge surface of said right and left portions of said frame and said upper edge of said right and left regions of said lens include cooperating means to secure said lens to said frame; said flexible plastic material of said frame enabling a snap-in engagement and a snap-out disengagement of said securing means to and from one another.

2. A protective eyewear assembly as described by claim 1, wherein said cooper at ing means comprises a slot means on said upper edge surface of said right and left portions of said frame and of protection means on said upper edge of said right and left regions of said, said projection means being so dimensioned a s to fit into said slot means.

3. A protective eyewear assembly as described by claim 1, wherein said retaining means comprises a rib means extending along an outer edge of a portion of said lower edge supporting surface of said right and left portions of said frame.

4. A protective eyewear assembly as described by claim 1, wherein said lens includes an integral side shield extension on each said right and left sight regions, the rearmost edge of said side shield extensions disposed inwardly of said upper edge extremities to enable said ear sterns to move to said inwardly folded position.

5. A protective eyewear assembly comprising:

a frame having right and left portions defining respective right and left apertures and a central bridging portion between said right and left portions; said right and left portions and said bridging portion including an upper edge surface and a lower edge surface; and a lens piece adapted to be mounted between said upper and lower edges of said frame, said lens piece including an upper portion configured to mate with at least a portion of said upper edge surface of said frame, and a lower edge configured to be supported on at least a portion of said lower edge surface of said frame;

wherein said lower edge surface of said frame includes at least one lens supporting wall portion and wherein at least one of said upper edge surface of said frame and said upper edge of said lens includes a projection receivable in an aperture provided in the other of said upper edge surface of said frame and said upper edge of said lens.

6. The eyewear in accordance with claim 5, wherein said frame is sufficiently flexible to enable snap-in engagement and a snap-out disengagement of said lens and said frame.

7. The eyewear in accordance with claim 6, wherein said frame is a flexible plastic material.

8. The eyewear in accordance with claim 5, wherein said lens comprises a flexible plastic material.

9. The eyewear in accordance with claim 5, wherein said lens piece includes a pair of right and left sight regions and a bridging section, and wherein at least one portion of each of an upper edge of said right and left sight regions are configured to mate with corresponding portions of said upper edge surface of said frame.

10. The eyewear in accordance with claim 9, wherein said lens piece includes a central bridging region, and wherein at least one portion of an upper edge of said bridging region is configured to mate with at least one portion of said upper edge surface of said frame.

11. The eyewear in accordance with claim 5, further comprising a pair of ear stems respectively mounted at an upper edge extremity of said right and left frame portions, wherein said ear stems are configured to pivot between an inwardly folded position and an outwardly ear contacting position.

12. The eyewear in accordance with claim 11, wherein said ear stems are configured to move in a vertical plane relative to a horizontal axis between said ear stem connection points of said frame.

* * * * *